United States Patent
Chen et al.

(10) Patent No.: US 11,319,267 B2
(45) Date of Patent: May 3, 2022

(54) METHOD FOR PREPARING 2-METHYLALLYL CHLORIDE FROM 1,2-DICHLOROISOBUTANE

(71) Applicants: ZHEJIANG UNIVERSITY, Zhejiang (CN); ZHEJIANG HUANGMA TECHNOLOGY CO., LTD., Zhejiang (CN)

(72) Inventors: Zhirong Chen, Hangzhou (CN); Hong Yin, Hangzhou (CN); Xinrong Wang, Shaoxing (CN); Yifeng Jin, Shaoxing (CN); Xingjun Zhao, Shaoxing (CN); Nan Dong, Shaoxing (CN); Meijun Zhang, Shaoxing (CN); Yuanrong Yu, Shaoxing (CN); Yuejiang Zhang, Shaoxing (CN)

(73) Assignees: ZHEJIANG UNIVERSITY, Hangzhou (CN); ZHEJIANG HUANGMA TECHNOLOGY CO., LTD., Shaoxing (CN)

( * ) Notice: Subject to any disclaimer, the term of this patent is extended or adjusted under 35 U.S.C. 154(b) by 12 days.

(21) Appl. No.: 16/759,860

(22) PCT Filed: Oct. 10, 2018

(86) PCT No.: PCT/CN2018/109598
§ 371 (c)(1),
(2) Date: Apr. 28, 2020

(87) PCT Pub. No.: WO2019/153774
PCT Pub. Date: Aug. 15, 2019

(65) Prior Publication Data
US 2021/0363076 A1    Nov. 25, 2021

(30) Foreign Application Priority Data
Feb. 9, 2018 (CN) .......................... 201810134166.0

(51) Int. Cl.
C07C 17/25 (2006.01)
C07C 17/383 (2006.01)
(Continued)

(52) U.S. Cl.
CPC ............ *C07C 17/25* (2013.01); *C07C 17/383* (2013.01); *C07C 17/386* (2013.01)

(58) Field of Classification Search
CPC ...................................................... C07C 17/25
See application file for complete search history.

(56) References Cited

U.S. PATENT DOCUMENTS

| 4,870,220 A | 9/1989 | Jabrik et al. |
| 2012/0302803 A1 | 11/2012 | Yamashita et al. |

FOREIGN PATENT DOCUMENTS

| BE | 448885 A | 2/1943 |
| CN | 1030407 A | 1/1989 |

(Continued)

OTHER PUBLICATIONS

BE448885A—translation, Feb. 28, 1943; pp. 1-2 (Year: 1943).*

(Continued)

*Primary Examiner* — Medhanit W Bahta
(74) *Attorney, Agent, or Firm* — Maschoff Brennan

(57) ABSTRACT

The present invention relates to a method for preparing 2-methylallyl chloride from 1,2-dichloroisobutane. The method is characterized in that 1,2-dichloroisobutane and a sodium hydroxide aqueous solution are used as raw materials; reactive rectification is performed in a combined rectifying tower to eliminate hydrogen chloride so as to obtain 2-methylallyl chloride. A plate tower is provided at the lower part of the combined rectifying tower; a packing tower is provided at the upper part of the combined rectifying tower; an inner reflux condenser is provided at the top of the combined rectifying tower. The sodium hydroxide aqueous solution is added from a first plate of the plate tower; and 1,2-dichloroisobutane is added from the middle part of the plate tower. The method has the advantages that (Continued)

the raw material 1 and 1,2-dichloroisobutane is fully converted; the selectivity of the 2-methylallyl chloride is high.

8 Claims, 1 Drawing Sheet

(51) Int. Cl.
*C07C 21/067* (2006.01)
*C07C 17/386* (2006.01)

(56) References Cited

FOREIGN PATENT DOCUMENTS

| | | |
|---|---|---|
| CN | 1288119 A | 3/2001 |
| CN | 1634818 A | 7/2005 |
| CN | 101182279 A | 5/2008 |
| CN | 202044960 U | 11/2011 |
| CN | 105669359 A | 6/2016 |
| CN | 107082738 A | 8/2017 |
| CN | 108299151 A | 7/2018 |
| DE | 3402446 A1 | 7/1985 |

OTHER PUBLICATIONS

CN Office Action and Search Report dated Feb. 27, 2019 as received in Application No. 201810134166.0.
CN Office Action dated Jul. 8, 2019 as received in Application No. 201810134166.0.

\* cited by examiner

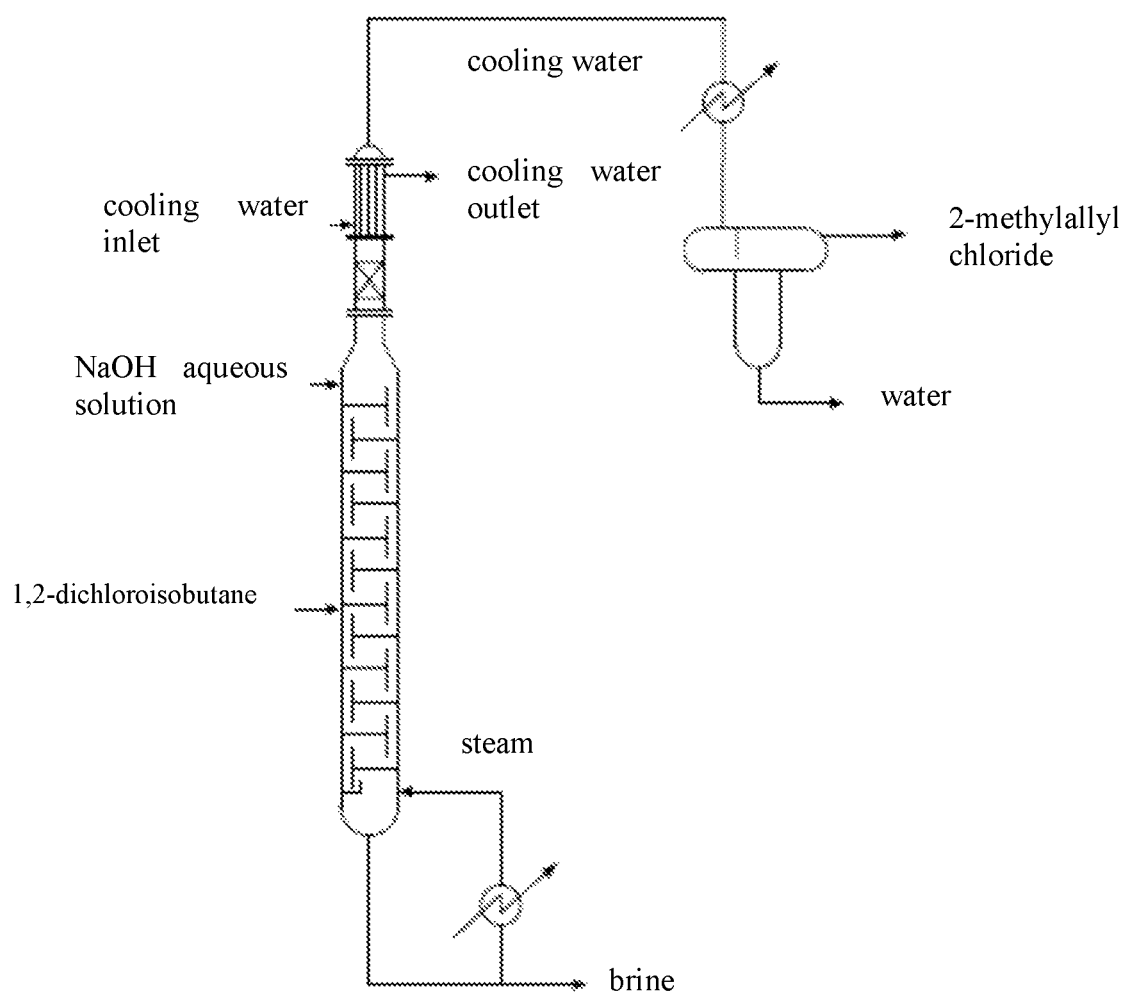

METHOD FOR PREPARING 2-METHYLALLYL CHLORIDE FROM 1,2-DICHLOROISOBUTANE

TECHNICAL FIELD

The invention relates to a dehydrochlorination reaction of organic matters, belongs to the field of organic synthesis reactions, and more particularly relates to a method for preparing 2-methylallyl chloride by dehydrochlorination of 1,2-dichloroisobutane.

BACKGROUND ART

2-Methylallyl chloride is an important intermediate for organic synthesis and is widely used in medicine, pesticides, perfume monomers, polymer materials and other fields.

2-Methylallyl chloride is generally obtained by a gas-phase chlorination reaction of isobutylene with chlorine gas. For example, in DE3402446, CN1030407, CN1288119, CN101182279, and CN202044960, an isobutylene gas-phase chlorination reaction is adopted to prepare 2-methylallyl chloride.

Various side reactions occur during the chlorination reaction. In addition to the main product 2-methylallyl chloride, the reaction products usually include a certain amount of chloro-tert-butane, isobutenyl chloride, 1,2-dichloroisobutane and 3,3'-dichloro-isobutylene and other side products. Among them, 1,2-dichloroisobutane and 3,3'-dichloro-isobutylene are polychlorinated by-products, are free of direct application field, and need to be treated as hazardous wastes. In the separation process of chlorination reaction liquid, the polychloride is generally discharged as a high-boiling-point component from the tower bottom of the last tower of a multi-tower continuous rectifying tower.

The simplest separation process is two-tower continuous rectification, which separates low-boiling-point substances from the top of the first tower and separates high-boiling-point substances from the second tower ("Industrial Production Technology of Methallyl Chloride with an Annual Output of 1,000 tons", Nanjing Meishan Chemical Plant, 1995).

CN1288119 employs a five-tower process to discharge high-boiling-point substances from a fifth tower.

None of the existing literatures mentions the effective use of high-boiling-point substances.

SUMMARY OF THE INVENTION

In view of the problem of effective utilization of high-boiling-point substances, the inventors of the present invention propose a method to separate 1,2-dichloroisobutane from high-boiling-point substances, and then prepare 2-methallyl chloride from 1,2-dichloroisobutane and a sodium hydroxide aqueous solution. This method can not only realize waste utilization, but also has high reaction selectivity.

A method for preparing 2-methallyl chloride from 1,2-dichloroisobutane, wherein 1,2-dichloroisobutane and a sodium hydroxide aqueous solution are used as raw materials, and react in a rectifying tower to eliminate hydrogen chloride, and the product 2-methallyl chloride is rectified from the top of the rectifying tower.

The sodium hydroxide aqueous solution has a concentration of 10-20%; and a mass ratio of the sodium hydroxide aqueous solution to the 1,2-dichloroisobutane is 1.6-3.5:1.

An azeotrope of the 2-methallyl chloride and water is obtained from the top of the rectifying tower, and is layered by cooling to obtain the 2-methallyl chloride.

The rectifying tower is a combined rectifying tower, wherein a plate tower is provided at the lower part of the combined rectifying tower; a packing tower is provided at the upper part of the combined rectifying tower; an inner reflux condenser is provided at the top of the tower top; and a reboiler is provided at the bottom of the combined rectifying tower to provide a heat source.

The number of plates in the plate tower on the lower part of the combined rectifying tower is 10-20; and the upper packing tower has 10-20 theoretical plates.

A tray of the plate tower is a sieve tray, a bubble tray or a float valve tray; and the packing tower is structured packing or random packing.

The sodium hydroxide aqueous solution is added from a first plate of the plate tower of the combined rectifying tower, and the 1,2-dichloroisobutane is added from the fifth to fifteenth plates in the middle of the plate tower on the lower part of the combined rectifying tower.

The reflux ratio of a reflux in the tower top is controlled to 1-5.

The inventors of the present invention have through researches found that in the presence of alkaline, chlorine on the tertiary carbon of 1,2-dichloroisobutane is more likely to undergo a elimination reaction than chlorine on a 1-position, and the eliminated hydrogen chloride reacts with sodium hydroxide to generate sodium chloride, and the reaction product is 2-methallyl chloride (i.e., 2-methylallyl chloride). However, if the formed 2-methylallyl chloride cannot leave a basic reaction system in time, it will continue to undergo hydrolysis and etherification reactions to form 2-methylallyl alcohol and 2-methylallyl ether, thereby reducing the reaction selectivity. To this end, the present invention proposes to adopt a reactive rectification method (a reaction in a rectifying tower) to carry out the elimination reaction. The product 2-methylallyl chloride is removed from the reaction system in time by taking advantage of the fact that the boiling point of the product is about 30° C. lower than that of the reactants and the product can form a binary azeotrope with water, thereby greatly improving the selectivity of the elimination reaction. After the binary azeotrope is cooled, the organic phase is layered into an organic phase, i.e., 2-methallyl chloride. Studies have also found that this elimination reaction requires a certain residence time. Therefore, the present invention uses the plate tower as a reactor for the elimination reaction.

Effects of the Invention

According to the present invention, reactive rectification is adopted, such that 1,2-dichlorot-butane and a sodium hydroxide aqueous solution are subjected to a hydrogen chloride elimination reaction to obtain 2-methylallyl chloride. The reaction selectivity is high, and the by-product 1,2-dichloroisobutane is converted into the product 2-methylallyl chloride.

BRIEF DESCRIPTION OF THE DRAWINGS

The FIGURE is a schematic diagram of a combined reactive rectification device and a reaction process flow thereof according to the present invention.

DETAILED DESCRIPTION

The technical solution of the present invention will be further described below with reference to the examples.

The separation process of 1,2-dichloroisobutane feedstock required by the present invention is as follows:

high-boiling-point substances (about 80% of 1,2-dichloroisobutane and about 20% of 3,3'-dichloro-isobutene) are continuously added to the middle of a continuous rectifying tower with 20 theoretical plates, and a ratio ratio on the tower top is controlled to about 1.0. The 1,2-dichloroisobutane produced from the tower top accounts for 79.8% of the feed, has a content of 99.8% or more. 3,3'-Dichloro-isobutylene is obtained from the tower bottom with a content of about 99%.

As shown in the FIGURE, in the combined rectifying tower of the present invention, a reboiler is provided at the bottom to provide a steam heat source, and a plate tower is provided at the lower part of the combined rectifying tower. The sodium hydroxide aqueous solution is added from a first plate of the plate tower on the lower part of the combined rectifying tower, and 1,2-dichloroisobutane is added from the fifth to the fifteenth plates in the middle of the plate tower on the lower part of the combined rectifying tower. A packing tower is provided on the upper part of the combined rectifying tower, and a reflux condenser is provided at the tower top. Using water as a cold source, an azeotrope of 2-methylallyl chloride and water rectified from the top of the combined tower is cooled by the condenser and introduced into a layerer. The organic phase is 2-methallyl chloride. Brine is discharged from the tower bottom of the combined rectifying tower.

Example 1

As shown in the FIGURE, a sodium hydroxide aqueous sodium having a concentration of 20% is continuously added to a first plate on the lower part of a combined rectifying tower (20 sieve trays are provided at the lower part of the tower, and random packing with a number of theoretical plates of 10 is provided at the upper part of the tower). 1,2-Dichloroisobutane is continuously added to a fifteenth plate. A mass ratio of the sodium hydroxide aqueous solution to the 1,2-dichloroisobutane is 1.6, and the reflux ratio at the tower top is controlled to 5. The steam from the tower top is condensed and layered by a layerer. The amount of the organic phase on the upper layer is 71.2% of the amount of the 1,2-dichloroisobutane feedstock. Gas chromatography analysis shows that the content of 2-methylallyl chloride in the organic phase is 99.3%, and the yield is 99.2%. Brine is discharged from the tower bottom, wherein the content of organic matters is less than 0.04%.

Example 2

As shown in the FIGURE, a sodium hydroxide aqueous sodium having a concentration of 10% is continuously added to a first plate on the lower part of a combined rectifying tower (10 sieve trays are provided at the lower part of the tower, and random packing with a number of theoretical plates of 20 is provided at the upper part of the tower). 1,2-Dichloroisobutane is continuously added to a fifth plate. A mass ratio of the sodium hydroxide aqueous solution to the 1,2-dichloroisobutane is 3.5, and the reflux ratio at the tower top is controlled to 1. The steam from the tower top is condensed and layered by a layerer. The amount of the organic phase on the upper layer is 71.1% of the amount of the 1,2-dichloroisobutane feedstock. Gas chromatography analysis shows that the content of 2-methylallyl chloride in the organic phase is 99.2%, and the yield is 99.0%. Brine is discharged from the tower bottom, wherein the content of organic matters is less than 0.05%.

Example 3

As shown in the FIGURE, a sodium hydroxide aqueous sodium having a concentration of 15% is continuously added to a first plate on the lower part of a combined rectifying tower (15 sieve trays are provided at the lower part of the tower, and random packing with a number of theoretical plates of 15 is provided at the upper part of the tower). 1,2-Dichloroisobutane is continuously added to a tenth plate. A mass ratio of the sodium hydroxide aqueous solution to the 1,2-dichloroisobutane is 3, and the reflux ratio at the tower top is controlled to 3. The steam from the tower top is condensed and layered by a layerer. The amount of the organic phase on the upper layer is 71.3% of the amount of the 1,2-dichloroisobutane feedstock. Gas chromatography analysis shows that the content of 2-methylallyl chloride in the organic phase is 99.6%, and the yield is 99.6%. Brine is discharged from the tower bottom, wherein the content of organic matters is less than 0.03%.

The invention claimed is:

1. A method for preparing 2-methallyl chloride from 1,2-dichloroisobutane, wherein 1,2-dichloroisobutane and a sodium hydroxide aqueous solution are used as raw materials, and react in a rectifying tower to eliminate hydrogen chloride, and the product 2-methallyl chloride is rectified from the top of the rectifying tower.

2. The method according to claim 1, wherein the sodium hydroxide aqueous solution has a concentration of 10-20%; and a mass ratio of the sodium hydroxide aqueous solution to the 1,2-dichloroisobutane is 1.6-3.5:1.

3. The method according to claim 1, wherein an azeotrope of 2-methallyl chloride and water is obtained from the top of the rectifying tower, and is layered by cooling to obtain 2-methallyl chloride.

4. The method according to claim 1, wherein the rectifying tower is a combined rectifying tower, a plate tower is provided at the lower part of the combined rectifying tower; a packing tower is provided at the upper part of the combined rectifying tower; an inner reflux condenser is provided at the top of the combined rectifying tower; and a reboiler is provided at the bottom of the combined rectifying tower to provide a heat source.

5. The method according to claim 4, wherein the number of plates in the plate tower on the lower part of the combined rectifying tower is 10-20; and the upper packing tower has 10-20 theoretical plates.

6. The method according to claim 5, wherein a tray of the plate tower is a sieve tray, a bubble tray or a float valve tray; and the packing tower is structured packing or random packing.

7. The method according to claim 5, wherein the sodium hydroxide aqueous solution is added from a first plate of the plate tower of the combined rectifying tower, and the 1,2-chloro-tert-butane is added from the fifth to fifteenth plates in the middle of the plate tower on the lower part of the combined rectifying tower.

8. The method of claim 1, wherein the reflux ratio of a reflux in the tower top is controlled to 1-5.

* * * * *